US012582646B2

(12) United States Patent
Sadee

(10) Patent No.: US 12,582,646 B2
(45) Date of Patent: Mar. 24, 2026

(54) METHOD FOR TREATING DRUG OR ALCOHOL DEPENDENCY

(71) Applicant: AETHER THERAPEUTICS INC., Austin, TX (US)

(72) Inventor: Wolfgang Sadee, Ross, CA (US)

(73) Assignee: Aether Therapeutics Inc., Austin, TX (US)

( * ) Notice: Subject to any disclaimer, the term of this patent is extended or adjusted under 35 U.S.C. 154(b) by 1016 days.

(21) Appl. No.: 17/417,309

(22) PCT Filed: Jan. 3, 2020

(86) PCT No.: PCT/US2020/012107

§ 371 (c)(1),
(2) Date: Jun. 22, 2021

(87) PCT Pub. No.: WO2020/142644

PCT Pub. Date: Jul. 9, 2020

(65) Prior Publication Data

US 2022/0047580 A1 Feb. 17, 2022

Related U.S. Application Data

(60) Provisional application No. 62/788,167, filed on Jan. 4, 2019.

(51) Int. Cl.
| | |
|---|---|
| *A61K 31/485* | (2006.01) |
| *A61P 25/36* | (2006.01) |
| *C07D 491/107* | (2006.01) |

(52) U.S. Cl.
CPC ............ *A61K 31/485* (2013.01); *A61P 25/36* (2018.01); *C07D 491/107* (2013.01)

(58) Field of Classification Search
None
See application file for complete search history.

(56) References Cited

U.S. PATENT DOCUMENTS

| | | | | |
|---|---|---|---|---|
| 6,713,488 B2 * | 3/2004 | Sadee | .................. | A61K 31/485 |
| | | | | 514/282 |
| 8,748,448 B2 * | 6/2014 | Sadee | .................. | A61K 31/137 |
| | | | | 514/282 |

| | | | | |
|---|---|---|---|---|
| 9,775,840 B2 | 10/2017 | Blumberg et al. | | |
| 10,925,870 B2 | 2/2021 | Sadee et al. | | |
| 2001/0049375 A1 | 12/2001 | Sadee et al. | | |
| 2003/0211157 A1 | 11/2003 | Simon | | |
| 2004/0024006 A1 | 2/2004 | Simon | | |
| 2009/0111844 A1 | 4/2009 | Sadee et al. | | |
| 2011/0071163 A1 | 3/2011 | Woodward | | |
| 2013/0090350 A1 * | 4/2013 | Sadee | .................. | A61K 45/06 |
| | | | | 514/282 |

FOREIGN PATENT DOCUMENTS

| | | |
|---|---|---|
| WO | 2008075997 A1 | 6/2008 |
| WO | 2017120417 A1 | 7/2017 |

OTHER PUBLICATIONS

Nicholls et.al. ((2010), Opioid Dependence Treatment and Guidelines, JMCP, 16, S14-S21 (Year: 2010).*
The English translation of the Chinese Office Action, mailed on Dec. 14, 2023, in the related Chinese Appl. No. 202080018736.5.
The English translation of the Japanese Office Action, mailed on Sep. 29, 2023, in the related Japanese Appl. No. 2021-539143.
The English translation of the Chinese Office Action, mailed on May 31, 2023, in the related Chinese Appl. No. 202080018736.5.
Stromberg et al. "A comparison of the effects of 6-beta naltrexol and naltrexone on the consumption of ethanol or sucrose using a limited access procedure in rats." Pharmacol Biochem Behav May 2002;72(1-2):483-90.
Rukstalis et al., "6-beta-naltrexol reduces alcohol consumption in rats," Alcohol Clin Exp Res Oct. 2000;24(10):1593-6.
The International Search Report and Written Opinion, mailed on Apr. 1, 2020, in the corresponding PCT Appl. No. PCT/US2020/012107.
US Office Action, mailed on May 11, 2023, in U.S. Appl. No. 17/180,945.
The English translation of the Chinese Office Action, mailed on Jun. 4, 2024, in the related Chinese Appl. No. 202080018736.5.
Examination report No. 1, mailed on Sep. 20, 2024, in the related Australian Appl. No. 2020205097.

* cited by examiner

*Primary Examiner* — Juliet C Switzer
*Assistant Examiner* — Dawanna Shar-Day White

(57) ABSTRACT

Provided herein is a method for weaning a subject suffering from a drug addiction or addictive behaviors involving opioid signaling by sequentially blocking peripheral and CNS opioid receptors and modulating opioid dependence.

7 Claims, No Drawings

METHOD FOR TREATING DRUG OR ALCOHOL DEPENDENCY

CROSS-REFERENCE TO RELATED APPLICATIONS

This application claims priority from U.S. provisional application Ser. No. 62/788,167 filed on Jan. 4, 2019, which is expressly incorporated herein by reference in its entirety.

CROSS-REFERENCE TO RELATED APPLICATIONS

This application is a National Stage Application of PCT/US2020/012107 filed on Jan. 3, 2020, which claims priority from U.S. Provisional Patent Application No. 62/788,167 filed on Jan. 4, 2019. Each of prior mentioned applications is hereby expressly incorporated by reference herein in its entirety.

FIELD OF THE INVENTION

The invention is directed to a drug addiction weaning protocol, such as an opioid weaning protocol and an alcohol weaning protocol, or weaning from addictive behaviors where opioid signaling is involved.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Drug addiction and other addictive behaviors represent a serious societal problem. The recent epidemic of opioid induced fatal overdosing highlights the urgency of addressing addiction. Other drug use disorders and addictive behaviors appear also to involve opioid signaling activated indirectly, leading to treatment with opioid antagonists such as naltrexone. (See *Br J Pharmacol.* 2015 August; 172(16): 3964-79. doi: 10.1111/bph.13190. Epub 2015 Jun. 26. The opioid receptors as targets for drug abuse medication. Noble F[1,2,3], Lenoir M[1,2,3], Marie N•Predictors of Naltrexone Response in a Randomized Trial: Reward-Related Brain Activation, OPRM1 Genotype, and Smoking Status. Schacht J P[1], Randall P K[1], Latham P K[1], Voronin K E[1], Book S W[1], Myrick H[1,2], Anton R F[1] *J Med Toxicol.* 2016 March; 12(1):71-5. doi: 10.1007/s13181-015-0512-x. Naltrexone: Not Just for Opioids Anymore. Sudakin D[1]).

Weaning opioid addicted subjects (subjects with opioid use disorder) has proven difficult, hampered by strong abstinence withdrawal and high recidivism. Typical opioid antagonists cause severe induced withdrawal even if given in gradually increasing doses. Research has shown that induced opioid withdrawal at very low doses of clinically used antagonists results from suppression of spontaneous opioid receptor activity (inverse agonism), with the antagonist acting in a non-competitive fashion (as an inverse agonist) (1,6,7,8). At higher doses, designed to block the opioid agonist at the receptor in a competitive fashion, such opioid antagonists cause additional withdrawal symptoms. Following withdrawal, these typical antagonists (such as naloxone, naltrexone, and nalmefene) can be given in a stable opioid antagonist maintenance dosing schedule to prevent further opioid abuse. However, these typical opioid antagonists (those acting as inverse agonists) elicit aversion even in a portion of non-opioid-addicted persons; for example, the use of naltrexone to ameliorate alcohol addiction is limited in part because of aversive effects in a portion of subjects, leading to non-compliance. Also important, these typical antagonists have instant access to the brain and cause opioid withdrawal by acting simultaneously on central and peripheral opioid receptors, leading to severe overall antagonist induced opioid withdrawal symptoms. It was determined in mice that naltrexone was equally potent in blocking peripheral and central opioid analgesic effects even when given orally as it readily enters the central nervous system through the blood-brain-barrier (7), and naltrexone has exceptional potency in blocking central opioid effects in mice, guinea pigs, rhesus monkeys, and humans (2,6,7,9,10).

Previous research has identified neutral opioid antagonists that potently inhibit the activation of opioid receptors by agonists (opioid analgesics), without suppressing spontaneous receptor signaling, which appears to be a hallmark of the dependent state and is elevated in it. Previous results show that constitutively active MOR receptors can maintain an opioid dependent state by continuously signaling MOR receptors (Corder et al. 2013), and therefore contribute to persistent relapse issues. As a result, neutral opioid antagonists cause less severe withdrawal, and only at higher doses designed to compete with the opioid antagonist at the receptor. For example, in opioid dependent mice, a neutral antagonist even at high doses fails to elicit any withdrawal 24 hours after the last morphine dose (when all morphine is eliminated), whereas naloxone and naltrexone still cause robust withdrawal by suppressing spontaneous receptor activity (Raehal K M, Lowery J J, Bhamidipati C M, Paolino R M, Blair J R, Wang D, Sadée W, Bilsky E J. (2005) In vivo characterization of 6beta-naltrexol, an opioid ligand with less inverse agonist activity compared with naltrexone and naloxone in opioid-dependent mice. J Pharmacol Exp Ther. 313, 1150-1162). Moreover, the neutral opioid antagonist 6-beta-naltrexol (6BN) can actually prevent naloxone (inverse agonist) induced withdrawal jumping in acutely morphine-dependent mice—a key benchmark for a neutral opioid antagonist. In addition, research has shown that naloxone and naltrexone derived antagonists with a reduced C-6-OH or C-6-NH$_2$ function not only act as neutral opioid antagonists but also appear to be extruded from the brain by export transporters in the blood brain barrier (BBB), thereby gaining peripheral selectivity. For example, 6BN is tenfold less potent in mice (Yancey Wrona et al. 2009 Yancey-Wrona J E, Raymond, T J, Mercer, H K, Sadee, W, and Bilsky, E J (2009) 6bnaltrexol preferentially antagonizes opioid effects on gastrointestinal transit compared to antinociception in mice. Life Sci 85, 413-420.), and at least tenfold less potent in humans (11), in blocking opioid drug antinociception (centrally mediated) than blocking opioid effects on the gastrointestinal tract. Moreover, 6BN is ~100-fold less potent that naltrexone in blocking opioid antinociception in rhesus monkeys (10) and in guinea pigs (Porter et al. 2002 Porter S J, Somogyi A A, White J M (2002) In vivo and in vitro potency studies of 6beta-naltrexol, the major human metabolite of naltrexone. Addict. Biol. 7:219-225.

These results have led to the conclusion that 6BN as the main metabolite of naltrexone does not substantially contribute to its central effects on opioid receptors; however, the molecular properties of this type of neutral opioid antagonist have not been considered in this conclusion. For example, 6BN has been shown to be highly potent in preventing the development of opioid dependence in morphine treated juvenile mice, at dose levels not expected to block conventional morphine effects such as antinociception (Oberdick et al. (2016)). In this study, morphine was co-injected s.c. with increasing doses of 6beta-naltrexol for several days, and dependence was subsequently tested with naloxone-induced withdrawal jumping. 6beta-Naltrexol significantly reduced naloxone-withdrawal jumping at 0.02 mg/kg co-injected with 20 mg/kg morphine. Internal unpublished results show that a dose as low as 0.01 mg/kg 6beta-naltrexol given together with morphine or methadone similarly reduces or prevents subsequent opioid withdrawal in mice and guinea pigs, supporting the notion that low dose 6beta-naltrexol affects dependence at opioid agonist doses below those that block CNS mediated analgesia. These results indicate that treatment of opioid subjects taking opioid drugs with low 6BN doses could reverse opioid dependence while not causing CNS mediated withdrawal acutely, nor block opioid analgesia. In addition, Corder et al. (2017) have shown that a peripherally selective opioid antagonist prevents opioid-induced hyperalgesia, a key element in opioid tolerance requiring increasing doses to maintain analgesia. Taken together, these results indicate that the apparent peripheral selectivity of 6BN is caused by two mechanisms, first having relatively restricted access to the brain and second binding with high affinity to distinct mu opioid receptor conformations with different prevalence in the CNS and the periphery, and distinct roles in opioid dependence. 6BN and its analogues can therefore be considered as peripherally selective neutral opioid antagonists that interact potently with distinct forms of the mu opioid receptor that are involved in dependence and hyperalgesia, involving basal mu receptor signaling, thereby modulating the opioid dependent state—they are dependence modulators. This finding is relevant to treatment of any addictive condition involving enhanced opioid receptor signaling with 6BN and its analogues acting at high potency. (See Corder G, Doolen S, Donahue R R, Winter M, Jutras B, He Y, Hu X, Wieskopf J S, Mogil J S, Storm D R, Wang Z J, McCarson K E, and Taylor B K, Constitutive μ-opioid receptor activity leads to long-term endogenous analgesia and dependence. *Science* 2013; 341, 1394-1399; Corder G, Tawfik V L, Wang D, Sypek E I, Low S A, Dickinson J R, Sotoudeh C, Clark J D, Barres B A, Bohlen C J, Scherrer (2017). Loss of μ opioid receptor signaling in nociceptors, but not microglia, abrogates morphine tolerance without disrupting analgesia. Nat Med. 23:164-173; J. Oberdick, Y. L., M. A. Phelps, M. S. Yudovich, K. Schilling, and W. Sadee. Preferential delivery of an opioid antagonist to the fetal brain in pregnant mice. J. Pharmacol. Exp. Ther. 358: 22-30 (2016). PMID: 27189967).

A need exists in the art, therefore, for an effective strategy to wean an opioid addict from opioid abuse without the limiting adverse effects seen in the art, and to suppress the influence of upregulated mu opioid receptor signaling on addictive conditions involving an opioid component such as alcoholism. It is understood that the proposed treatments do not exclude currently acceptable interventions designed to facilitate opioid withdrawal or weaning from other addictive drugs and behaviors, but rather can serve as an additional tool supporting such interventions.

SUMMARY OF THE INVENTION

The invention is directed to a drug addiction weaning protocol. For weaning from opioid use disorder, the protocol first blocks peripheral opioid receptors with a peripherally selective neutral antagonist starting with a low dose to avoid strong withdrawal in a dependent subject, followed by an increasing dosage level in a stabilization period designed largely to inhibit peripheral opioid receptors while sparing central opioid receptors. As recent results indicate that this second dosage level can prevent or modulate opioid hyperalgesia and dependence, in addition to blocking peripheral adverse opioid effects, the opioid agonist dosage can be reduced without incurring withdrawal in this second phase, designed to lower the opioid drug burden. A further third step involves subsequent complete weaning by increasing doses of the antagonist that penetrate sufficiently into the brain to inhibit acute effects on central opioid receptors and by reducing and eliminating the opioid agonist. An optional fourth step involves an opioid antagonist maintenance dosage. For treatment of other addictive conditions, including other addictive drugs such as alcohol use disorder, and stimulants and nicotine dependence, or addictive behaviors such as eating disorders and gambling, involving indirect activation of opioid signaling pathways in the central nervous system but not in the periphery, the first treatment step with a very low dose of a peripherally selective neutral antagonist can be deleted as peripheral opioid receptors are not sensitized by high circulating levels of opioid drugs so that neutral antagonist doses acting peripherally are well tolerated.

Thus, provided is a method of weaning an opioid-dependent subject from an opioid addiction, comprising the sequential steps of:

a) blocking peripheral opioid receptors in said subject by administering a therapeutically effective amount of at least one peripherally-selective neutral opioid receptor antagonist to said subject to block said peripheral opioid receptors;

b) stabilizing peripheral opioid receptor signaling developed in the dependent state by maintaining administration of the peripherally selective neutral opioid antagonist at doses sufficient to block peripheral but not central opioid receptors, thereby, reducing hyperalgesia and opioid dependence, while reducing the dosage of the opioid agonist; and c) blocking activation of CNS opioid receptors by opioid drugs or endogenous opioids in said subject by adjusting the dosage of said opioid receptor antagonist, and in parallel reducing and ceasing opioid agonist treatment, thereby weaning said subject from said opioid addiction.

A further fourth step may include implementing a maintenance strategy designed to prevent relapse by continuous administration of an antagonist, a preferred embodiment comprising a neutral opioid antagonist at dosages to reach the brain, or for long-term preventive treatment with an intermediate dose of said antagonist designed to block activation of only peripheral opioid receptors while reducing tolerance and dependence.

Further provided is a method of reducing reinforcing processes, under conditions of other drug addictions such as alcoholism, and addictive behaviors such as eating disorders, involving opioid signaling, representing an opioid dependent state driven by spontaneously/basally active mu opioid receptors, by reversing the opioid dependent-like state at low doses of a peripherally selective neutral antagonist, and at higher doses preventing acute opioid signaling in the CNS, for example during binge drinking, comprising the sequential steps of:

a) reversing enhanced basal mu opioid receptor signaling developed during addictive drugs and behaviors by release of endogenous opioids, by administration of the peripherally selective neutral opioid antagonist at doses sufficient to block acute activation of peripheral but not central opioid receptors, and sufficient to reverse a dependent tolerant state driven by basally active mu opioid receptors; and b) blocking CNS opioid receptors in said subject by adjusting the maintenance dosage of said opioid receptor antagonist, thereby blocking the acute reinforcing actions of opioid signaling in the CNS during exposure to addictive drugs other than opioids such as alcoholism, and addictive behaviors such as eating disorders.

A further fourth step may include implementing a long-term maintenance strategy designed to prevent relapse by continuous administration of an antagonist, a preferred embodiment comprising a peripherally selective neutral opioid antagonist at dosages to reach the brain during a time period of high risk of recidivism, or at lower doses over prolonged times to reduce persistent risk of relapse.

DETAILED DESCRIPTION OF THE INVENTION

It is to be understood that the descriptions of the present invention have been simplified to illustrate elements that are relevant for a clear understanding of the present invention, while eliminating, for the purpose of clarity, many other elements found in typical pharmaceutical compositions and methods of stabilization. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The instant invention is directed to an opioid addiction (opioid use disorder, OUD) weaning protocol, and addiction to other drugs and addictive behaviors involving opioid signaling. The protocol uses a peripherally selective opioid antagonist, for example, 6beta-naltrexol (1,2), to first block peripheral opioid agonist actions and reverse the dependent state of the opioid receptor system, and then, at increasing doses, to block acute opioid effects in the central nervous system ("CNS") until the enforcing processes of addiction have subsided, reducing the risk of recidivism. In the specific case of opioid drug use disorder, severe withdrawal symptoms are one of the main obstacles to successful weaning, while long-term sustained drug seeking behavior is the primary cause of recidivism. Withdrawal can be measured by multiple symptoms, such as pulse rate, GI upset, sweating, tremor, yawning and pupil size. The Clinical Opioid Withdrawal Scale (COWS; comprising 11 symptoms) is typically used to measure withdrawal (3). Inhibiting peripheral opioid receptors reverses opioid effects in multiple organs, including the gastrointestinal tract, kidneys, immune cells, and osteoblast. Typical peripheral withdrawal symptoms include gastrointestinal cramping, accelerated bowel movements, and diarrhea—symptoms that serve to titrate the 6-beta-naltrexol dosage until the patient no longer experiences peripheral withdrawal symptoms. Continued 6beta-naltrexol dosing will result in gradual reversal of the dependent state in the periphery, while it also appears to reverse the dependent state of central opioid mu opioid receptor signaling at doses that do not prevent opioid drug induced analgesia. Withdrawal symptoms mediated by opioid antagonists (naloxone and naltrexone, which readily enter the brain and act as inverse agonists, i.e., they also suppress spontaneous receptor signaling) are severe even at very low doses and include both central and peripheral effects that appear to potentiate each other, including seizures and violent gastrointestinal events. Therefore, the withdrawal and weaning symptoms expected for 6beta-naltrexol—as a neutral opioid antagonist causing inherently less withdrawal than the inverse agonist naloxone and naltrexone—is manageable first for peripheral effects and subsequently at higher doses that penetrate the blood-brain-barrier to block also acute central opioid effects, monitored with measures of discomfort the patient registers, and more exactly the COWS scale. Blocking the peripheral opioid receptor first can have the additional advantage of interrupting a vicious cycle of interactions between opioid receptors on afferent nociceptors (peripheral, in an ascending pathway) and CNS receptors reported to contribute to hyperalgesia—a cause of increasing opioid dosages needed to reach the desired effects (an aspect of tolerance) (4,5). As a neutral antagonist, 6beta-naltrexol has one additional advantage over inverse agonists such as naltrexone: it allows basal opioid receptor signaling, which has been shown to have physiological relevance and drives opioid dependence when upregulated (13), and is instrumental in recovery from hypersensitivity/hyperalgesia induced by latent sensitization causing sustained inflammatory pain in rats (14). On the other hand, reversal of opioid dependence by low doses of 6beta-naltrexol indicates that the increased abundance of a mu opioid receptor form responsible for elevated basal signaling in the dependent state is depleted by 6beta-naltrexol—acting as a dependence modulator—to favor a receptor form lacking basal signaling activity.

Since addictive drugs other than opioids, and addictive behaviors, also involve opioid signaling indirectly, one can surmise that release of endogenous opioids generates a similar opioid dependent state of the mu opioid receptor which can then drive and enforce such addictive behaviors. In these cases, a peripherally selective neutral opioid antagonist such as 6beta-naltrexol can be given at low doses sufficient to block peripheral opioid receptors without causing withdrawal but sufficient to reverse the opioid dependent receptor state also in the CNS, followed by higher doses that also block acute endogenous opioid effects in the CNS, further reducing the rewarding effects of such behaviors during acute episodes. Long-term administration of such antagonist can be either at this later high dose, or at the initial low dose to prevent the long-lasting conditions promoting the addictive behavior. The advantage over naltrexone—a medication tested in the treatment of many addictive conditions—lies in the continued basal mu opioid receptor signaling at physiological levels, while preventing increased basal signaling known to play a role in role in dependence, hyperalgesia, and neuropathic pain.

In one embodiment of the invention related to opioid use disorder, the weaning protocol with 6beta-naltrexol involves a 4-step process: step 1: gradual weaning of the peripheral opioid system; step 2: stabilization period with an intermediate dose of 6-beta-naltrexol, and dose reduction of the opioid analgesic as acceptable to the patient; step 3; initiation of complete withdrawal by increasing doses of 6-betanaltrexol that can reach the brain while decreasing and eliminating opioid analgesic dosages; step 4: maintenance with high doses of 6beta-naltrexol to prevent relapse, with no opioid analgesic administered. In this last step, alternative established means of maintenance are feasible, for example slow release naltrexone as currently used; however, high dose 6-beta-naltrexol maintenance has the potential to be more effective in balancing the non-dependent opioid system by allowing basal (ligand-free) opioid receptor signaling, which is blocked by inverse agonists. (13, 14). If pain therapy continues to be necessary after completion of step 2, the patient can be administered a combination preparation of an opioid analgesic with a dose of 6beta-naltrexol that does not block CNS-mediated opioid analgesia but prevents dependence and opioid-induced hyperalgesia and can reduce addiction liability. Thus, the invention provides for the stepwise process of weaning to alleviate withdrawal and facilitate abstinence, taking advantage of opioid physiology and the unique properties of a peripherally selective neutral opioid antagonist such as 6beta-naltrexol, or analogues and derivatives with similar properties.

Upregulation of mu opioid receptor signaling in other addiction conditions, such as alcoholism, leads to a general embodiment of treatment with 6beta-naltrexol to reduce the opioid dependent receptor state and at higher doses prevent acute increase of opioid signaling triggered by release of endogenous opioid peptides. As a result of the indirect activation of endogenous opioid signaling in the brain, the peripheral opioid receptor system is less affected compared to opioid drug-induced dependence, and the first step of titrating 6beta-naltrexol at very low doses is not needed. Thus, intermediate doses of 6beta-naltrexol (step 2 in the opioid weaning protocol) are not expected to cause any withdrawal or aversion, as experienced with naltrexone by a substantial portion of subjects with alcohol use disorder, limiting the utility of naltrexone.

Research has determined that the naltrexone metabolite 6beta-naltrexol is a neutral opioid antagonist (the parent naltrexone is an inverse agonist in the dependent state), and moreover, is peripherally selective (in contrast to naltrexone which enters the brain readily) (1), therefore, providing the opportunity to prevent peripheral opioid side effects, such as opioid induced bowel dysfunction/constipation (OIC). Unexpectedly, such peripherally selective dosage levels of 6beta-naltrexol also reduce hyperalgesia and general dependence, with potential to lower opioid dosing and reduce withdrawal symptoms. Because 6-beta-naltrexol has sufficient access to the brain at higher doses to block acute opioid effects, and it has a longer half-life than typical opioid analgesics (9), naltrexol can accumulate under abuse conditions and thereby reduce addiction liability when formulated in an agonist/antagonist combination dosage. These findings have resulted in the following patents/applications all of which are expressly incorporated by reference: U.S. Pat. No. 8,748,448; U.S. Ser. No. 14/278,576; European Patent No. EP2214672; U.S. Ser. No. 12/288,347; European Patent No. 2214672; U.S. Ser. No. 10/544,083; U.S. Pat. Nos. 8,883,187; and 9,061,024.

Research in the art, however, has not addressed a strategy of how an individual on opioid pain therapy or an opioid addict can be weaned from opioid use, abuse, or from opioid maintenance programs, typically with methadone or buprenorphine. The inventors have discovered that any weaning protocol requires consideration of both peripheral and central opioid signaling, and their interactions, in the dependent state, which results in severe withdrawal symptoms upon cessation of opioid use or administration of conventional opioid antagonist (inverse agonists that act both centrally and peripherally with equal potency). A peripherally selective neutral antagonist in essence separates the acute opioid effects of central and peripheral opioid receptors, and disrupts interaction among them while causing acceptable peripheral withdrawal symptoms and re-establishing regular physiological functions (9,11). Recent evidence indicates that blocking peripheral opioid receptors prevents opioid induced hyperalgesia (4,5), which is at least in part a cause of opioid tolerance and leads to the need for increasing doses of opioids and enhanced dependence; however, effects on drug seeking behavior and intensity of opioid withdrawal remain uncertain, in subjects where the peripheral opioid receptor system has been blocked previously. Research in methadone maintenance subjects has shown that a single dose of 6-beta-naltrexol at intravenous doses of 0.5-1 mg can reverse opioid induced constipation with tolerable peripheral side effects and no central withdrawal symptoms (11). Lastly, and relevant to the weaning protocol proposed here, a dose of 6beta-naltrexol selective for blocking acute opioid drug effects at peripheral opioid receptor without preventing opioid analgesia appears sufficient to reverse or prevent opioid dependence, presumably by depleting with high potency the enhanced basally active mu opioid receptor form charactering the dependent state. This result indicates that opioid withdrawal is further alleviated.

Opioid receptors exist throughout multiple brain regions, typically protected by the formidable blood-brain barrier, which excludes some opioid compounds from entering the brain (the central nervous system) (12), or it reduces access to the CNS as observed with 6beta-naltexol. These opioid receptors are called here CNS opioid receptors. Peripheral organs such as the gastrointestinal tract, kidney, immune cells, vas deference, and more, also carry opioid receptors termed here peripheral opioid receptors with diverse physiological functions. Among the three main receptor types, mu, delta, and kappa, the mu opioid receptors are most relevant to analgesia and addictions, while the other subtypes also contribute. When referring to opioid antagonist, we imply here antagonism at the mu opioid receptor, while the antagonists in this invention typically also inhibit delta and kappa receptors to varying degrees, because of the similarity between opioid receptor subtypes. Selectivity for the mu receptor alone is not a requirement for this invention.

Peripheral opioid receptors, including mu, delta and kappa opioid receptors, are present in many tissues including the gastrointestinal tract, where they slow bowel movements and regulate fluid and electrolyte balance. These receptors are defined as those residing outside the blood-brain-barrier (BBB), consisting of tight endothelial cell layers around blood vessels in the brain, endowed with potent transporters that extrude a variety of substances from the brain, including opioids—but to substantially varying degrees as a function of their chemical structure. While structurally similar to, but in contrast to naltrexone, 6beta-naltrexol is largely excluded from the brain at low doses that saturate peripheral opioid receptors, owing to the reduction of the C-6 position and tilting of the ring structure resulting in interaction with extrusion pumps in the blood-brain-barrier—a feature shared between analogues with the same C-6 reduction. Nevertheless, 6beta-naltrexol appears to act with high potency in reversing opioid dependence—mediated centrally—at low doses that fail to block acute opioid effects (such as centrally mediated analgesia), suggesting the presence of a receptor form linked to dependence. Central opioid receptors reside in the brain with the BBB, with the mu opioid receptor (OPRM or MOR) the main target of opioid analgesics, and the main gauge for opioid addiction. Upon chronic opioid use, both peripheral and central opioid receptors, their cellular signaling pathways, and neuronal networks are altered to lead to a dependent and tolerant state. The interactions between peripheral and central signaling pathways have been studied only recently but appear to play a critical role in maintaining the opioid dependent/tolerant state, and a state of hyperalgesia (4,5). The weaning protocol in this invention defines a process designed to enable reversal of the dependent/tolerant state with tolerable withdrawal symptoms, and to maintain abstinence from opioid abuse thereafter. Similarly, reversing an opioid dependent state arising indirectly from drug use disorders other than OUD, and addictive behaviors, with 6beta-naltrexol and its analogues has the potential to reduce such addictive behaviors by removing a contributing driving force.

Both the peripheral and central opioid receptor systems are highly activated in the opioid dependent state, and both interact by influencing opioid tolerance, dependence, and likely also craving—all key elements of opioid addiction. The novel strategy first to suppress the peripheral opioid system must reflect its activated state, so that even a neutral opioid antagonist must be titrated in slowly in OUD (displacing a small fraction of an opioid agonist already can cause a physiological reaction). The same holds for subsequently weaning the central opioid receptor system when a 6-beta-naltrexol/opioid narcotic-analgesic regimen is given, except that in the absence of agonist—dependent peripheral opioid receptor signalling, and thereby reduction of opioid induced hyperalgesia, a dose reduction of the 6-beta-naltrexol/opioid narcotic-analgesic regimen may be feasible in a portion of subjects (as a result of reduced tolerance and dependence), thereby reducing overall exposure to the opioid. Full withdrawal can then be achieved by increasing the 6-beta-naltrexol dosage and phasing out the 6-beta-naltrexol/opioid narcotic-analgesic dosage, followed by continued dosing of 6beta-naltrexol.

This overall 4-step method of weaning in carefully orchestrated fashion is novel as it is the first to disrupt intentionally the interaction between peripheral and central opioid signalling, targeting hyperalgesia and dependence—an area only recently becoming a focus in biomedical research. Blocking the peripheral opioid receptor system with 6-beta-naltrexol has a number of additional benefits if a prolonged 6beta-naltrexol/opioid analgesic is medically needed, for example suppression of opioid effects on the GI tract, opioid induced bone loss, immune disruption, renal effects, and more. Following the initial titration with 6beta-naltrexol, a preferred 6beta-naltrexol/opioid agonist regimen is a combination formulation taken orally, as specified in the patents on combination products. In treating other drug use disorders and addictive behaviors, the peripheral opioid receptor system is unlikely to be activated so that the first step of treating OUD with very low doses of 6beta-nitrexol to avoid peripheral withdrawal symptoms is not needed.

In one embodiment, the invention can be used to treat alcohol addiction. The endogenous opioid system is involved in multiple types of addictive conditions and behaviors, in addition to opioid use disorders (OUD). Specifically, alcohol use disorder (AUD) is linked to aberrant opioid signalling akin to that observed in OUD, and shows overlap with parallel opioid and alcohol use disorders (OAUD). As a result, opioid antagonists such as naltrexone and nalmefene have been tested and shown to be effective not only to prevent narcotics abuse but also to reduce AUD, including binge drinking, while the efficacy of nalmefene is less well documented, with a substantial degree of treatment discontinuation. To prevent recidivism in OUD and ameliorate AUD, extended release formulations of naltrexone have been developed (XRNTX) capable of maintaining naltrexone blood levels>1 ng/ml for months, and successful in preventing OUD and reducing AUD. Naltrexone is metabolized to 6beta-naltrexol, which reaches blood levels 5-10 fold higher than those of naltrexone, because of its longer half-life. Whether 6beta-naltrexol contributes to or mediates the effect of naltrexone has yet to be determine definitively, as 6beta-naltrexol is considered to be less potent than naltrexone in antagonizing the acute effects of opioid analgesics (>100-fold less in guinea pigs and nonhuman primates), and it has slightly lower affinity to the mu opioid receptor (MOR) than naltrexone measured in vitro. This view was reinforced by results from a study comparing the effects of 6beta-naltrexol with naltrexone on alcohol consumption (rats do not metabolize naltrexone to 6beta-naltrexol), showing that 6beta-naltrexol is 25-fold less potent than naltrexone. However, in that study, the antagonists are given 15 min before the alcohol consumption test to rats habituated to high alcohol consumption, Stromberg M F, Rukstalis M R, Mackler S A, Volpicelli J R, O'Brien C P (2002). A comparison of the effects of 6-beta naltrexol and naltrexone on the consumption of ethanol or sucrose using a limited-access procedure in rats. Pharmacol Biochem Behav 72:483-490 to block acute reinforcing effects of drinking alcohol (Strromberg et al.).

Demonstrated in the present invention, 6beta-naltrexol has very high potency in preventing an opioid dependent state when given concomitantly with the opioid over several days before dependence is assessed. This high potency can be attributed to the ability 6beta-naltrexol to maintain or re-establish MOR conformational states/equilibrium germane to the non-dependent state—we therefore call 6beta-naltrexol an addiction or dependence modulator. 6beta-Naltrexol appears to exert its effect on modulating the addictive state in a non-competitive fashion at low doses—proposed here for the first time. While 6beta-naltrexol is effective at low doses, it can be given at increasing doses that inhibit acute effects of opioids peripherally and centrally (drugs and endogenous opioids), but the low-dose paradigm is designed to prevent or reverse the addictive state in which basal activity of the mu opioid receptor MOR drives long-term dependence and its sequelae.

When treating alcoholism with XRNTX, some evidence supports the view that its metabolite 6beta-naltrexol contributes to the clinical outcome (reduced alcohol consumption), as the degree of 'liking' alcohol in test subjects was correlated with 6beta-naltrexol levels. However, naltrexone itself is extremely potent and acts as an inverse agonist, with preferential binding to a basally active MOR characteristic of the dependent state. As alcohol consumption activates the endogenous opioid system indirectly, it is assumed that MOR will exist in this basally active dependent state in AUD that then itself drives further alcohol use. Therefore, 6beta-naltrexol can be effective at low doses that would not be considered active as a conventional antagonist because such low doses would fail to antagonize acute central opioid agonist effects. If 6beta-naltrexol indeed contributes to the efficacy of naltrexone in reducing alcoholism, this could prove advantageous over nalmefene, which cannot be metabolized to a neutral antagonist similar to the structure of 6beta-naltrexol (nalmefene has a C-6 C=C bond that is not reduced metabolically), but distinctions between naltrexone and nalmefene are still unclear ((Yelel-Okouma et al. 2017). *Fundam Clin Pharmacol.* 2017 October; 31(5):574-579. doi: 10.1111/fcp.12286. Epub 2017 May 9. Opioid substitution therapy or hidden opioids are a minefield for nalmefene: an atypical case series of 11 patients in Lorraine. Yéléhé-Okouma M[1], Martini H[2], Lemarié J[3], Labroca P[4], Petitpain N[1], Gibaja V[5], Paille F[2], Gillet P[1].))

Taken together, results indicate that low-dose 6beta-naltrexol will be effective in modulating the dependent state of the opioid receptor system, thereby reducing compulsory alcohol consumption in AUD, and in other conditions with upregulated basal MOR signaling.

In a particular embodiment of this invention, 6beta-naltrexol is given at doses sufficiently high to antagonize acute opioid effects in the CNS, either caused by opioid drugs or through release of endogenous opioids. This approach serves to prevent recidivism during a high-risk period after cessation of addictive drug use; however, long-term, this approach can lead to anhedonia and low compliance. For example, 6beta-naltrexol prevents both alcohol and sucrose intake acutely, but only at high doses (17). Preventing an opioid-dependent state with low doses 6beta-naltrexol is proposed here to be preferable for long-term interventions.

While 6-beta-naltrexol is one compound that is useful for the weaning protocol, other naltrexol and naloxol derivatives, analogs, and/or metabolites, such as those specified in U.S. Pat. No. 8,748,448, U.S. Ser. No. 14/278,576, European Patent No. EP2214672 and U.S. Ser. No. 12/288,347 (all of which are expressly incorporated by reference, including routes of administration and sustained release formulations), also have neutral antagonist properties and the same structure as 6beta-naltrexol that is recognized by export pumps in the blood-brain barrier, indicating they can also be peripherally selective. The invention embodies usage of any of these compounds or derivatives or metabolites thereof. For example, 6alpha-naltrexol, 6alpha- and beta-naloxol and their derivatives (including PEGylated derivatives), and 6alpha/beta-naltrexamine and 6alpha/beta-naloxamine, and specifically 6beta-naltrexamide, all show neutral antagonism. 6beta-Natrexamide has also been shown to have strong peripherally selective activity (internal results). In combinations, any opioid analgesic is a feasible component, embodied in the combination patents mentioned above. An example is a combination product of oxycodone or hydrocodone with 6beta-naltrexol.

6beta-Naltrexol was also tested in 4 methadone replacement patients who were sensitive to 0.05 mg naloxone i.v. These subjects tolerated 6eta-naltrexol at IV doses of up to 1 mg, resulting in bowel movements and some additional peripheral, but no central, withdrawal symptoms (one subject opted out of the study after the 0.5 mg dose) [11, internal data obtained from AIKO Biotechnology]. These results show good pharmacological properties of 6eta-naltrexol even after a first dose of 6BN in highly dependent methadone patients, when typical opioid antagonists (naloxone and naltrexone) would cause severe withdrawal at equivalent doses.

Thus, in one embodiment of the invention, provided is a method of weaning a drug-dependent subject from a drug dependency, comprising the sequential steps of:

a) blocking a peripheral opioid receptor in said subject by administering to said subject in need thereof a therapeutically effective amount of at least one peripherally-selective opioid receptor antagonist to said subject to block said peripheral opioid receptors;

b) stabilizing the peripheral opioid receptor signaling by maintaining administration of the peripherally selective opioid antagonist at doses sufficient to block peripheral but not central opioid receptors, preventing peripheral opioid adverse effects and resulting in reduction of opioid-induced hyperalgesia and dependence, while reducing the dosage of the opioid agonist;

c) blocking a CNS opioid receptor in said subject by adjusting the dosage of said opioid receptor antagonist, and in parallel reducing and ceasing opioid agonist treatment, thereby weaning said subject from said opioid addiction; and d) administering a maintenance dose with said antagonist at doses sufficient to block central opioid receptors during periods of high relapse risk and at intermediate dose sufficient to block peripheral opioid receptors long-term at doses sufficient to block activation of peripheral opioid receptors.

In one embodiment, the peripheral opioid receptor is the mu opioid receptor.

In one embodiment, the drug addiction is alcohol addiction or other drug use disorders such as nicotine and stimulants involving upregulated opioid receptor signaling in a state similar to opioid dependence, further including hyperalgesia and chronic neuropathic pain.

In one embodiment, said peripherally-selective opioid receptor antagonist is a neutral peripherally-selective opioid receptor antagonist.

In one embodiment, said neutral peripherally-selective opioid receptor antagonist is 6alpha/beta-naltrexol or 6alpha/beta-naloxol, 6alpha/beta-naltrexamine or 6alpha/beta-naloxamine, or an analog, derivative or metabolite thereof.

In one embodiment, in step a) blocking of said peripheral opioid receptors is measured by restoration of bowel activity in opioid use disorder without central opioid withdrawal symptoms.

In one embodiment, in step 1) the therapeutically effective amount of 6-beta-naltrexol is 0.5 to 40 mg.

In one embodiment, in step 1) 0.5 to 10 mg of 6beta-naltrexol is administered orally, once or twice daily for 2-4 days, followed by 2 to 20 mg once or twice daily for 4-8 days.

In one embodiment, in step 2) 4-50 mg of 6beta-naltrexol is administered orally, once or twice daily for 1-4 weeks or more, and the opioid agonist dose is reduced until first signs of abstinence symptoms emerge;

In one embodiment, in step 3) the dosage of said opioid receptor antagonist is increased in an amount sufficient to block said CNS opioid receptors, wherein 10-80 mg, preferably 20 mg, 6beta-naltrexol is administered orally twice daily for 4-8 days, then 20-120 mg, preferably 40 mg, once or twice daily for 1-4 weeks, and further escalation to range 40-300 mg, preferably 100 mg, once or twice daily for maintenance, while the opioid agonist dose is reduced and discontinued at a rate that elicits only mild, tolerable abstinence symptoms In one embodiment, said derivative or metabolite is 6beta-naltrexol.

In one embodiment, the method further comprises implementing an opioid antagonist maintenance regimen long-term until the risk of recidivism is considered low.

In one embodiment, in step 4) a 6-beta-naltrexol maintenance dose is administered long-term at a dosage range of 40-300 mg, preferably 100 mg, per day orally.

In one embodiment, for long-term maintenance with reduced risk of recidivism, the dosage of 6beta-naltresxol is reduced to 4-50 mg per day.

In one embodiment, provided is a method for the treatment of conditions other than opioid use disorder involving upregulated basal signaling of the mu opioid receptor (MOR) system in an individual in need thereof, comprising administration to the individual of a therapeutically effective amount of 6beta-naltrexol.

In one embodiment, the condition involving upregulated basal signaling of the mu opioid receptor (MOR) system is alcohol use disorder, opioid dependence, hyperalgesia, chronic neuropathic pain, alcoholism, nicotine addiction, cocaine and stimulant abuse, anorexia, binge eating, gambling and excessive sexual behaviors, further including hyperalgesia and chronic neuropathic pain.

In one embodiment, the condition involving upregulated basal signaling of the mu opioid receptor (MOR) system is alcohol use disorder combined with opioid disorder.

In a further embodiment of the invention, provided is a method of weaning a subject from a drug use disorder or exhibiting addictive compulsory behaviors, associated with upregulated opioid receptor signaling, comprising the sequential steps of:

a) administering a therapeutically effective amount of at least one peripherally-selective opioid receptor antagonist to said subject (step 2) to modulate the opioid-receptor dependent state, the selected antagonist being highly potent in reversing or preventing the dependent state while causing minimal withdrawal;

b) selectively blocking peripheral opioid receptor signaling by maintaining administration of the peripherally selective opioid antagonist at doses sufficient to suppress opioid drug effects at peripheral but not central opioid receptors, to reverse the dependent signaling state of the mu opioid receptor;

c) blocking CNS opioid receptors in said subject by adjusting the dosage of said opioid receptor antagonist (step 3), to prevent acute endogenous opioid signaling during addictive behavior episodes (optionally in parallel reducing and ceasing opioid agonist treatment, thereby weaning said subject from said opioid addiction); and d) long-term administering of said opioid receptor antagonist at doses (step 4), first at a sufficiently high dose effective in preventing recidivism of drug use or addictive behaviors by rendering opioid drugs ineffective, and later at a low dose (step 2) to prevent or reverse dependence.

The invention will now be further described in the Examples below, which are intended as an illustration only and do not limit the scope of the invention.

EXAMPLES

The inventors exploited the purposeful separation of the peripheral and central opioid receptor systems to ameliorate immediate withdrawal symptoms and to facilitate long lasting abstinence. The current invention, thus, provides for a multi-step opioid addiction weaning protocol using a peripherally selective neutral opioid antagonist, for example, 6beta-naltrexol, in a first step to block the peripheral opioid receptor system. In a second step, stabilization at an intermediate 6beta-naltrexol dosage allows for gradual reversal of the dependent state of the peripheral opioid system—potentially lasting for several weeks—which also allows for a reduction of the opioid agonist dose as hyperalgesia subsides. Moreover, such an intermediate dose appears also to reverse a dependent opioid receptor state in the CNS at doses insufficient to block acute opioid effects such as analgesia. If continued pain therapy is needed after completion of step 2 or any other time, an opioid analgesic/6-beta-naltrexol combination product designed to reduce peripheral side effects and addiction liability is the preferred embodiment. Step 3 involves applying increasing 6beta-naltrexol doses, gradually dampening opioid effects centrally, while opioid analgesics are gradually discontinued, with tolerable withdrawal symptoms if performed over a sufficient time period—for example two weeks. Administration of increasing doses of 6-beta-naltrexol will further reduce the danger of relapse as opioid agonists become relatively ineffective centrally—hence, administration of 6beta-natrexol is needed during this third weaning process (rather than opioid dose reduction alone) to prevent relapse during weaning (inverse agonists would still cause substantial withdrawal at this stage). In an additional step 4, to prevent relapse long-term after opioid cessation, with continuing high risk of relapse, 6beta-naltrexol is then administered at high doses sufficient to block any opioid effect both peripherally and centrally. For long-term treatments, an intermediate dose of 6beta-naltrexol sufficient to block peripheral opioid receptors (step 2) may be preferred embodiments, interfering minimally with physiological roles of the opioid system. Other long-term strategies are also feasible after complete withdrawal, for example slow release naltrexone preparations. When treating other drug addictions or addictive behaviors involving opioid signaling, the low dose 6beta-naltrexol dose (step 1) can be deleted as peripheral withdrawal is not expected t\o occur.

Example 1

Blocking of Peripheral Opioid Receptors. Step 1

This step applies to opioid use disorders. A slowly increasing dose of 6beta-naltrexol is administered orally in an amount sufficient to gradually overcome peripheral opioid effects in an addicted/dependent subject, leading to mild withdrawal characterized by restored bowel activity without excessive cramping or diarrhea, without central withdrawal symptoms. The recommended initial dose is 2 mg naltrexol orally (assuming ~30% oral bioavailability; estimated dosage range 0.5-10 mg), once or twice daily for 2-4 days, followed by 6 mg once or twice daily for 4-8 days (estimated dosage range 2-20 mg twice daily). Step 1 is designed to suppress peripheral effects of the opioid drug with minimal peripheral withdrawal symptoms, and reverse at least partially opioid dependence.

Example 2

Stabilization of Peripheral Opioid Receptor Signaling. Step 2

Step 1 is followed by 6-beta-naltrexol administration 10 mg once or twice daily (estimated dosage range 4-50 mg twice daily) for 1-4 weeks. This dose can be maintained to prevent peripheral side effects and reverse hyperalgesia and the dependent opioid state of peripheral opioid receptors. As opioid induced hyperalgesia is expected to be reversed at least in part during step 2, the dose of the opioid agonist should be reduced and maintained at a lower dose if no withdrawal symptoms appear. The goal is to reduce the burden of opioid exposure during step 2.

Patients requiring continued pain therapy after completing step 2 can be administered a maintenance dose consisting of a 6-beta-naltrexol/opioid analgesic combination preparation, containing 6-beta-naltrexol doses sufficient to block peripheral effects without interfering with opioid analgesia, while reducing addiction liability, as described in the combination formulation patents. Patients willing to undergo further weaning from opioid use, whether taking opioids as part of pain therapy, under opioid use disorder, or in opioid maintenance programs (methadone and buprenorphine), progress to step 3 of the weaning protocol.

Example 3

Blocking of CNS Opioid Receptors and Complete Weaning. Step 3

Increasing doses of 6-beta-naltrexol after blocking the peripheral opioid receptors are given to the subject to gradually inhibit the CNS effects of opioid analgesics. Recommended doses are 20 mg (range 10-80 mg) once or twice daily for 4-8 days, then 40 mg (range 20-120 mg) once or twice daily for 1-4 weeks, and if necessary, further escalation to 100 mg (range 40-300 mg) once or twice daily for maintenance. A single dose of 20 mg naltrexol iv failed to block analgesia caused by 10 mg morphine iv in opioid naïve subjects; the IC50 for blocking morphine induced slowing of bowel movement was ~3 mg naltrexol iv; the peripheral/central potency ratio for naltrexol is ~10 in mice but may be higher in humans. In addition to increasing the dose of 6-beta-naltrexol, individuals will implement gradual cessation of opioid dosing altogether. Dosing schedules can be facilitated by designing sustained release formulations as described in preceding incorporated patents.

Example 4

Antagonist Maintenance Therapy after Complete Opioid Weaning to Prevent Relapse. Step 4

Opioid antagonist maintenance with 6-beta-naltrexol may require 100 mg (dosage range 40-300 mg) per day orally (assuming 20-40% bioavailability). After weaning, alternative preventive maintenance protocols (for example with naltrexone sustained release) can be substituted for 6-beta-naltrexol in subjects who do not experience aversion to naltrexone. Any benefit of using 6beta-naltrexol (neutral antagonist) over naltrexone (inverse agonist) long-term requires further testing—with consideration of the physiological role of basal mu opioid receptor signaling in pain perception and dependence (13, 14). For long-term treatments, the lower dose of 6beta-naltrexol described in Step 3 might be preferable to minimize interference of physiological opioid functions while reducing opioid dependence. Ceasing opioid use altogether must be medically supervised for at least one year to determine the rate of recidivism.

Criteria of success in Step 1 include normalization of bowel functions without excessive withdrawal symptoms, leading to high compliance in taking 6beta-naltrexol. In step 2, 6-beta-naltrexol dose escalation is tolerated without further withdrawal symptoms (or only minimal symptoms), and ability to reduce the opioid agonist dosage without triggering withdrawal. In step 3, success will be measured by ability of the individual to undergo complete weaning with tolerable abstinence symptoms, and the success rate compared to other weaning procedures. Additional medications currently used to facilitate weaning (such as alpha-2 adrenergic agonists) can be added to the weaning step. In step 4, reduction of the rate of recidivism compared to standard withdrawal/maintenance strategies will be a measure of success.

Example 5

Treatment of Addiction to Other Drugs or of Addictive Behaviors

As these conditions indirectly involve enhanced opioid signaling and a dependent opioid state in the CNS contributing to the addiction, the same multi-step protocol of administering 6beta-naltrexol or its anaklogues and derivatives, can be applied—except that step 1 is no longer needed because peripheral adverse effects are not expected, and the risk of withdrawal in step 3 blocking CNS opioid receptors is minimal. Steps 2-4 are designed to modulate the mu opioid receptor state favoring one that predominates in an opioid non-dependent state, and at higher doses to prevent any effect of acute upregulation of endogenous opioid signaling. The treatment of alcohol addiction is a primary target for this treatment strategy, but other drug use disorders (e.g., nicotine, stimulants) and addictive behaviors can be similarly treated with 6beta-naltrexone and its analogues, with less aversive effects while maintaining physiological roles for spontaneous mu opioid receptor signalling in a non-dependent state.

The invention will be further described, without limitation, by the following numbered paragraphs:

1. A method of weaning a drug-dependent subject from a drug dependency, or an addictive behavior, comprising the sequential steps of:
   a) blocking a peripheral opioid receptor in said subject by administering to said subject in need thereof a therapeutically effective amount of at least one peripherally-selective neutral opioid receptor antagonist to said subject to block said peripheral opioid receptors;
   b) stabilizing the peripheral opioid receptor signaling to reduce opioid induced hyperalgesia and dependence, by maintaining administration of the peripherally selective neutral opioid antagonist at doses sufficient to block peripheral but not central opioid receptors, while reducing the dosage of the opioid agonist; and
   c) blocking a CNS opioid receptor in said subject by adjusting the dosage of said opioid receptor antagonist, and in parallel reducing and ceasing opioid agonist treatment, thereby weaning said subject from said opioid addiction.

2. The method according to paragraph 1, wherein the peripheral opioid receptor is the mu opioid receptor.

3. The method according to paragraph 1, wherein the drug addiction is alcohol addiction or opioid dependency, or addiction to other drugs of abuse including nicotine and stimulants.

3a. The method according to paragraph 1, wherein the addiction is a compulsory behavior such as eating disorders or gambling.

4. The method according to paragraph 1, wherein said peripherally-selective opioid receptor antagonist is a neutral peripherally-selective opioid receptor antagonist.

5. The method according to paragraph 4, wherein said neutral peripherally-selective opioid receptor antagonist is 6-beta-naltrexol or 6-beta-naloxol, or 6alpha-naltrexol or 6alpha-naloxol, or 6alpha/beta-naltrexamine or 6alpha/beta-naloxamine, or a derivative or metabolite thereof, including 6beta-naltrexamide.

6. The method according to paragraph 1, related to opioid use disorder, wherein in step 1) blocking of said peripheral opioid receptors is measured by restoration of bowel activity without central opioid withdrawal symptoms.

7. The method according to paragraph 1, related to opioid use disorder, wherein in step 1) the therapeutically effective amount of 6beta-naltrexol is 0.5 to 20 mg.

8. The method according to paragraph 1, related to opioid use disorder, wherein in step 1) 0.5 to 10 mg of 6beta-naltrexol is administered orally, twice daily for 2-4 days, followed by 2 to 20 mg once or twice daily for 4-8 days.

9. The method according to paragraph 1, related to opioid use disorder, wherein in step 2) 4-50 mg of 6-beta-naltrexol is administered orally, once or twice daily for 1-4 weeks or more, and the opioid agonist dose is reduced until first signs of abstinence symptoms emerge;

10. The method according to paragraph 1, related to opioid use disorder, wherein in step 3) the dosage of said opioid receptor antagonist is increased in an amount sufficient to block said CNS opioid receptors, wherein 10-80 mg, preferably 20 mg, 6-beta-naltrexol is administered orally twice daily for 4-8 days, then 20-120 mg, preferably 40 mg, twice daily for 1-4 weeks, and further escalation to range 40-300 mg, preferably 100 mg, once or twice daily for maintenance, while the opioid agonist dose is reduced and discontinued at a rate that elicits only mild, tolerable abstinence symptoms.

11. The method according to paragraph 5, wherein said derivative or metabolite is 6beta-naltrexol.

12. The method according to paragraph 1, further comprising step 4) of implementing a high dose opioid antagonist maintenance regimen long-term until the risk of recidivism is considered low.

13. The method according to paragraph 12, wherein in step 4) a 6beta-naltrexol maintenance dose is administered over time periods with high relapse risk at a dosage range of 40-300 mg, preferably 100 mg, per day orally, until long-term treatment at an intermediate dose can be continued, at a dose range of 4-50 mg per day once or twice when risk of recidivism has declined.

14. A method for the treatment of addictive conditions involving upregulated basal signaling of the mu opioid receptor (MOR) system in an individual in need thereof, comprising administration to the individual of a therapeutically effective amount of 6beta-naltrexol.

15. The method according to paragraph 14, wherein the condition involving upregulated basal signaling of the mu opioid receptor (MOR) system is alcohol use disorder, opioid dependence, hyperalgesia, chronic neuropathic pain, alcoholism, nicotine addiction, cocaine and stimulant abuse, anorexia, binge eating, gambling and excessive sexual behaviors.

16. The method according to paragraph 14, wherein the condition involving upregulated basal signaling of the mu opioid receptor (MOR) system is alcohol use disorder combined with opioid dependence.

17. A method of weaning an opioid-dependent subject from a drug addiction, or addictive behaviors comprising the sequential steps of:

a) administering a therapeutically effective amount of at least one peripherally-selective opioid receptor neutral antagonist to said subject to modulate the opioid dependent state, the selected antagonist being highly potent in reversing or preventing dependence while causing minimal withdrawal;

b) selectively blocking peripheral opioid receptor signaling by maintaining administration of the peripherally selective neutral opioid antagonist at doses sufficient to suppress opioid drug effects at peripheral but not central opioid receptors, while reducing a dependent opioid-like state, wherein 4-50 mg of 6-beta-naltrexol is administered orally, once or twice daily for 1-4 weeks or more;

c) blocking CNS opioid receptors in said subject by adjusting the dosage of said opioid receptor antagonist, thereby preventing endogenous opioids to activate central opioid receptors, wherein in step 4) a 6beta-naltrexol maintenance dose is administered long-term at a dosage range of 40-300 mg, preferably 100 mg, once or twice per day orally, thereby weaning said subject from said addiction; and d) long-term administering of said opioid receptor antagonist at an intermediate dose (step 2) can be continued, at a dose range of 4-50 mg per day once or twice when risk of recidivism has declined, effective in reducing the risk of recidivism.

REFERENCES

1. Sadee, W, Wang, D, and Bilsky, E J (2005) Basal opioid receptor activity, neutral antagonists, and therapeutic opportunities. Life Sci 76, 1427-1437.

2. Yancey-Wrona, J E, Raymond, T J, Mercer, H K, Sadee, W, and Bilsky, E J (2009) 6b-naltrexol preferentially antagonizes opioid effects on gastrointestinal transit compared to antinociception in mice. Life Sci 85, 413-420.

3. Wesson D R and Ling W (2003) The Clinical Opioid Withdrawal Scale (COWS). J Psychoact Drugs 35, 253-259.

4. Araldi D[1], Ferrari L F, Levine J D (2017) Hyperalgesic priming (type II) induced by repeated opioid exposure: maintenance mechanisms. Pain 158:1204-1216.

5. Corder G, Tawfik V L, Wang D, Sypek E I, Low S A, Dickinson J R, Sotoudeh C, Clark J D, Barres B A, Bohlen C J, Scherrer (2017). Loss of μ opioid receptor signaling in nociceptors, but not microglia, abrogates morphine tolerance without disrupting analgesia. Nat Med. 23:164-173.

6. Porter S J, Somogyi A A, White J M. (2002) In vivo and in vitro potency studies of 6beta-naltrexol, the major human metabolite of naltrexone. Addict Biol. 7, 219-225.

7. Raehal K M, Lowery J J, Bhamidipati C M, Paolino R M, Blair J R, Wang D, Sadée W, Bilsky E J. (2005). In vivo characterization of 6beta-naltrexol, an opioid ligand with less inverse agonist activity compared with naltrexone and naloxone in opioid-dependent mice. J Pharmacol Exp Ther. 313, 1150-1162.

8. Sirohi S, Dighe S V, Madia P A, Yoburn B C (2009) The relative potency of inverse opioid agonists and a neutral opioid antagonist in precipitated withdrawal and antagonism of analgesia and toxicity. J Pharmacol Exp Ther. 330, 513-519.

9. Yancey-Wrona, J, Dallaire, B, Bilsky, E, Bath, B, Burkart, J, Wenster, L, Magiera, D, Yang, X, Phelps, M, and Sadee, W. (2011) 6β-naltrexol, a peripherally selective opioid antagonist that inhibits morphine induced slowing of gastrointestinal transit: an exploratory study. Pain Medicine 12, 1727-1737.

10. Ko M C, Divin M F, Lee H, Woods J H, Traynor J R. (2006) Differential in vivo potencies of naltrexone and 6beta-naltrexol in the monkey. J Pharmacol Exp Ther. 316, 772-779.

11. Mendelson J, Li L, Flower K, Harris W, Coyle J R, et al. (2011) The Effects of 6β-Naltrexol, a Putative Neutral Opioid Antagonist, in Opioid-Dependent Subjects: A Proof-of-Concept Trial. *J Addict Res Ther* 2:108. doi: 10.4172/2155-6105.1000108. AIKO Biotechnology. A Phase-I, Two-Stage, Double-Blind, Placebo-Controlled, Pharmacokinetic and Pharmacodynamic Trial of Low Doses of Intravenous 6β-Naltrexol (AIKO-150) in Opioid-Dependent Subjects. *ClinicalTrials.gov.* January 2009.

12. Kalvass J C, Olson E R, Cassidy M P, Selley D E, Pollack G M. (2007) Pharmacokinetics and pharmacodynamics of seven opioids in P-glycoprotein-competent mice: assessment of unbound brain EC50, and correlation of in vitro, preclinical, and clinical data. J Pharmacol Exp Ther. 323, 346-355.

13. Corder G, Doolen S, Donahue R R, Winter M, Jutras B, He Y, Hu X, Wieskopf J S, Mogil J S, Storm D R, Wang Z J, McCarson K E, and Taylor B K, Constitutive μ-opioid receptor activity leads to long-term endogenous analgesia and dependence. *Science* 2013; 341,1394-1399.

14. Walwyn W M, Chen C, Kim H, Minasyan A, Ennes H S, McRoberts J A, Marvizon J C G. Sustained suppression of hyperalgesia during latent sensitization by_mu-, _delta-, and_kappa-opioid receptors and_2A-adrenergic receptors: role of constitutive activity. Neurobiol. Dis. 36:204-221 (2016).

It is to be understood that the invention is not limited to the particular embodiments of the invention described above, as variations of the particular embodiments may be made and still fall within the scope of the appended claims.

What is claimed is:

1. A method for weaning a drug-dependent subject from a drug dependency, wherein the drug dependency is an opioid addiction and wherein the subject is taking an opioid agonist as part of pain therapy, under opioid use disorder, or in a maintenance program, comprising the sequential steps of:

a) oral administration of a dose of 0.5 to 10 mg of 6-beta-naltrexol, once or twice daily for 2-4 days, followed by a dose of 2 to 20 mg once or twice daily for 4-8 days to block a peripheral opioid receptor in said subject;

b) oral administration of 4-50 mg of 6-beta-naltrexol, once or twice daily for at least 1-4 weeks, and reduction of the 6-beta-naltrexol dose until first signs of abstinence symptoms emerge, thereby stabilizing the peripheral opioid receptor signaling by maintaining administration of the 6-beta-naltrexol at doses sufficient to block peripheral but not central opioid receptors, to prevent peripheral opioid adverse effects and reduce opioid-induced hyperalgesia and dependence, during reduction of the dosage of the opioid agonist;

c) oral administration of 6-beta-naltrexol in an increasing amount to block a CNS opioid receptor in said subject, and during reduction and cessation of opioid agonist treatment at a rate that elicits only mild, tolerable abstinence symptoms, thereby weaning said subject from said opioid addiction, wherein the 6-beta-naltrexol is for oral administration in a dose of 10-80 mg twice daily for 4-8 days, then in a dose of 20-120 mg once or twice daily for 1-4 weeks, and further escalation to a maintenance dose of 40-300 mg once or twice daily; and d) administration of 6-beta-naltrexol of the maintenance dose to block central opioid receptors during periods of high relapse risk and at an intermediate dose sufficient to block activation of peripheral opioid receptors long-term.

2. The method according to claim 1, wherein the peripheral opioid receptor is the mu opioid receptor.

3. The method according to claim 1, wherein in step a) blocking of said peripheral opioid receptors is measured by restoration of bowel activity in opioid use disorder without central opioid withdrawal symptoms.

4. The method according to claim 1, further comprising implementation of a long-term opioid antagonist maintenance regimen until the risk of recidivism is considered low.

5. The method according to claim 4, wherein, in the long-term opioid antagonist maintenance regimen, the 6-beta-naltrexol is for administration at a dosage range of 40-300 mg per day orally.

6. The method according to claim 4, wherein in the long-term opioid antagonist maintenance regimen, the 6-beta-naltrexol is for administration at a dosage of 100 mg per day orally.

7. The method according to claim 4, wherein for long-term maintenance with reduced risk of recidivism, the dosage of 6-beta-naltrexol is reduced to 4-50 mg per day.

* * * * *